(12) United States Patent
Coulson et al.

(10) Patent No.: US 6,362,346 B1
(45) Date of Patent: Mar. 26, 2002

(54) PROCESS FOR THE PREPARATION OF α-METHYLENE-γ-BUTYROLACTONE AND α-ACETOXYMETHYL-γ-BUTYROLACTONE

(75) Inventors: Dale Robert Coulson, Wilmington, DE (US); David L. Thorn, West Chester; Mark A. Scialdone, Oxford, both of PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/710,974

(22) Filed: Nov. 10, 2000

Related U.S. Application Data

(60) Provisional application No. 60/165,042, filed on Nov. 12, 1999.

(51) Int. Cl.[7] .............................................. C07D 307/02
(52) U.S. Cl. ...................................... 549/295; 549/323
(58) Field of Search .................................. 549/295, 323

(56) References Cited

U.S. PATENT DOCUMENTS 5,166,357 A    11/1992   Orlek et al.  ................. 514/299

FOREIGN PATENT DOCUMENTS

JP         10-120672         5/1998

OTHER PUBLICATIONS

J. Martin, et al., A New method for the synthesis of Alpha–Methylenebutyrolactones, J. Chem. Soc., 1970, 1:27, Dow Chemical Company, Wayland, Massachusetts.

A. W. Murray, et al., Convenient Synthesis of Alpha–Epoxylactones (4–Oxo–1,5–dioxaspiro[2.4]heptanes and –[2.5]octanes), Synthesis, 1985, 1:35–38, University of Dundee, Scotland.

F. Gelman, et al., One–Pot Reactions with Opposing Reagents: Sol–Gel Entrapped Catalyst and Base, J. Am. Chem. Soc., 2000, Hebrew University of Jerusalem, Israel.

*Primary Examiner*—Amelia Owens
(74) *Attorney, Agent, or Firm*—Inna Belopolsky, Esq.

(57) ABSTRACT

This invention pertains to a process for making α-methylene-γ-butyrolactone by acid-catalyzed rearrangement of tetrahydro-3-furoic acid. In a further embodiment, when tetrahydro-3-furoic acid is treated with acetic anhydride and an acid catalyst, α-acetoxymethyl-γ-butyrolactone is produced in high yield. Under basic conditions, α-acetoxymethyl-γ-butyrolactone can readily formα-methylene-γ-butyrolactone by the elimination of acetic acid. These reactions provide α-methylene-γ-butyrolactone by novel routes which do not require butyrolactone or formaldehyde.

40 Claims, No Drawings

US 6,362,346 B1

PROCESS FOR THE PREPARATION OF α-METHYLENE-γ-BUTYROLACTONE AND α-ACETOXYMETHYL-γ-BUTYROLACTONE

This application claim benefit Prov. No. 60/165,042 filed Nov. 12, 1999.

FIELD OF THE INVENTION

This invention is in the field of synthetic organic chemistry. This invention pertains to simple, efficient and economic methods to produce α-methylene-γ-butyrolactone from tetrahydro-3-furoic acid and α-acetoxymethyl-γ-butyrolactone.

TECHNICAL BACKGROUND OF THE INVENTION

α-Methylenelactones have been the subject of intensive synthetic studies. Specifically, the α-methylene-γ-butyrolactone group is an important structural feature of many sesquiterpenes of biological importance. In addition, α-methylene-γ-butyrolactone, or its hydrogenated product, 3-methyltetra-hydrofuran, are regarded as a potential key monomers in both homopolymers and copolymers. Currently the cost of α-methylene-γ-butyrolactone is too high to warrant commercial production of its resulting polymers. Some of the current synthetic routes suffer from low yields, byproducts and expensive starting materials. In the instant invention, high yields of α-methylene-γ-butyrolactone are obtained by an acid-catalyzed rearrangement of tetrahydro-3-furoic acid or base-catalyzed reaction of α-acetoxymethyl-γ-butyrolactone.

An early synthesis of α-methylene-γ-butyrolactone involved two steps (Martin et al., *J. Chem. Soc. D* 1:27 (1970)). The first is carboxylation of γ-butyrolactone with methyl methoxymagnesium carbonate (Stiles' reagent) to produce the acid. Next, the acid is briefly treated with a mixture of aqueous formaldehyde and diethylamine, followed by a separate treatment of the crude product with sodium acetate in acetic acid. The first step requires 6–7 hours and affords almost quantitative yields, whereas the second step can be accomplished in less than 30 minutes but with yields of only 50%.

Murray et al. (*Synthesis* 1:35–38 (1985); see also U.S. Pat No. 5,166,357) disclose a route to α-methylene-γ-butyrolactone that also involves a two-step sequence consisting of the reaction of γ-butyrolactone with ethyl formate in the presence of base, followed by refluxing the resulting α-formyl-γ-butyrolactone sodium salt under nitrogen with paraformaldehyde in tetrahydrofuran. Distillation affords the desired α-methylene-γ-butyrolactone as a colorless oil. This reaction sequence can best be explained by formyl transfer from carbon to oxygen followed by elimination of carboxylate anion.

Essentially all approaches to α-methylene-γ-butyrolactone are liquid-phase processes. One exception is the vapor-phase process described in JP 10120672. Production of α-methylene-γ-butyrolactone comprises subjecting γ-butyrolactone or an alkyl-substituted γ-butyrolactone, in which one or more hydrogen atoms at the β- or γ-position of the γ-butyrolactone are substituted with $C_1$–$C_{18}$ alkyl groups, to a gaseous phase catalytic reaction using a raw material gas containing formaldehyde or its derivative in the presence of a catalyst. Molecular oxygen is preferably added to the raw material gas and the catalyst is preferably silica alumina catalyst. Specifically, a gaseous mixture of γ-butyrolactone, formaldehyde, water, nitrogen and oxygen was passed through a reactor packed with Wakogel C-200, pretreated with an aqueous potassium hydroxide solution and heating, at 330° C., to afford α-methylene-γ-butyrolactone at a conversion of 35.5% and a selectivity of 46.9%.

Although the above methods for the production of α-methylene-γ-butyrolactone are useful, they are time consuming and are multipart processes. Therefore, the problem to be solved is to find a simple and efficient method to produce α-methylene-γ-butyrolactone. The present methods represent an advance in the art by offering processes that are a single or double step with high yields and good selectivity.

SUMMARY OF THE INVENTION

The present invention provides a process for the preparation of α-methylene-γ-butyrolactone comprising heating a mixture of a furoic acid selected from the group consisting of tetrahydro-3-furoic acid and esters of tetrahydro-3-furoic acid, and a strong acid catalyst under conditions whereby α-methylene-γ-butyrolactone is formed and optionally recovering the α-methylene-γ-butyrolactone. Typically the acid catalyst is selected from the group consisting of fluorosulfonic acid, trifluoromethanesulfonic acid, sulfuric acid, benzenesulfonic acid, toluenesulfonic acid and phosphoric acid.

In an alternate embodiment the invention provides a process for preparing α-acetoxymethyl-γ-butyrolactone comprising heating a mixture of a furoic acid selected from the group consisting of tetrahydro-3-furoic acid and esters of tetrahydro-3-furoic acid, with acetic anhydride and a strong acid catalyst under conditions wherein α-acetoxymethyl-γ-butyrolactone is formed and optionally recovering the α-acetoxymethyl-γ-butyrolactone.

In another embodiment the present invention provides a process for preparing α-methylene-γ-butyrolactone comprising heating a mixture of a gaseous furoic acid selected from the group consisting of tetrahydro-3-furoic acid and esters of tetrahydro-3-furoic acid and a gas phase base catalyst under conditions whereby α-methylene-γ-butyrolactone is formed and optionally recovering the α-methylene-γ-butyrolactone. Gas phase catalysts may be supported on suitable supports such as silica for example.

The invention additionally provides a novel composition of α-acetoxy-methyl-γ-butyrolactone according to the formula

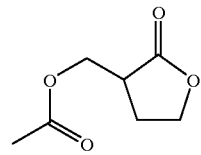

Another embodiment of the invention relates to a process for preparing α-methylene-γ-butyrolactone comprising heating a mixture of α-acetoxymethyl-γ-butyrolactone and base catalyst under conditions whereby α-methylene-γ-butyrolactone is formed and optionally recovering the α-methylene-γ-butyrolactone. Within the context of this embodiment the base catalyst may be any base which forms an acetate when reacted with acetic acid and is typically defined according to the formula, $M(acetate)_x$; where x is an integer selected from the group consisting of 1 and 2; and M is a cation of charge $+x$ selected from the group consisting of $Li^+$, $Na^+$, $K^+$, $Rb^+$, $Cs^+$, $Mg^{++}$, $Ca^{++}$, $Sr^{++}$, $Ba^{++}$, $(CH_3)$ $_4N^+$, $(C_2H_5)_4N^+$, $(CH_3)_4P^+$, $(C_2H_5)_4P^+$ and 1-ethyl-3-methylimidazolium cation.

The invention additionally provides a process for preparing α-methylene-γ-butyrolactone comprising: (a) combining a furoic acid selected from the group consisting of tetrahydro-3-furoic acid and an ester of tetrahydro-3-furoic acid with an acid anhydride and a strong acid catalyst under conditions whereby a α-carboxylatomethyl-γ-butyrolactone is formed; (b) heating the product of step (a) under conditions whereby α-methylene-γ-butyrolactone is formed; and (c) optionally recovering the α-methylene-γ-butyrolactone. Typically the production of α-carboxylatomethyl-γ-butyrolactone will occur at temperatures of about 20° C. to about 200° C. whereas the heating step will occur at temperatures of about 100° C. to about 400° C. Optionally a base catalyst may be added to the product of step (a) to effect the conversion of o-carboxylatomethyl-γ-butyrolactone to α-methylene-γ-butyrolactone. Under these conditions the temperature required for conversion is less, and will range from about 40° C. to about 200° C. Within the context of this embodiment the base catalyst may be defined according to the formula, $M(carboxylate)_x$ where x is an integer selected from the group consisting of 1 and 2; and M is a cation of charge +x chosen from the group consisting of $Li^+$, $Na^+$, $K^+$, $Rb^+$, $Cs^+$, $Mg^{++}$, $Ca^{++}$, $Sr^{++}$, $Ba^{++}$, $(CH_3)_4N^+$, $(C_2H_5)_4N^+$, $(CH_3)_4P^+$, $(C_2H_5)_4P^+$ and 1-ethyl-3-methylimidazolium cation; and carboxylate is selected from the group consisting of formate, acetate, propionate, benzoate, phthalate, poly(acrylate), succinate, monomethylsuccinate, 2,2'-dimethylsuccinate and 2,3-dimethylsuccinate.

DETAILED DESCRIPTION OF THE INVENTION

α-Methylene-γ-butyrolactone is useful as a key monomer in both homopolymers and copolymers. The instant invention pertains to a process for making α-methylene-γ-butyrolactone by acid-catalyzed rearrangement of tetrahydro-3-furoic acid (Scheme I). In an alternate embodiment, when tetrahydro-3-furoic acid or esters of tetrahydro-3-furoic acid are treated with acetic anhydride and an acid catalyst, α-acetoxymethyl-γ-butyrolactone is produced in high yield (Scheme II). Under either basic conditions, or high temperature (100° C.–400° C.) α-acetoxymethyl-γ-butyrolactone can readily form α-methylene-γ-butyrolactone by the elimination of acetic acid. Acid anhydrides other than acetic acid similarly can be used to form α-methylene-γ-butyrolactone within the scope of this embodiment. These reactions provide α-methylene-γ-butyrolactone by two novel routes which do not require butyrolactone or formaldehyde.

Scheme I

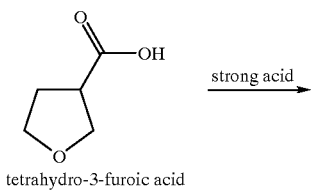
tetrahydro-3-furoic acid strong acid
→

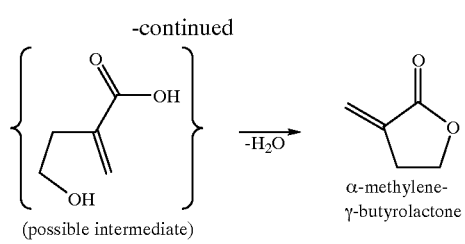
(possible intermediate)

−H₂O →

α-methylene-γ-butyrolactone

Scheme II

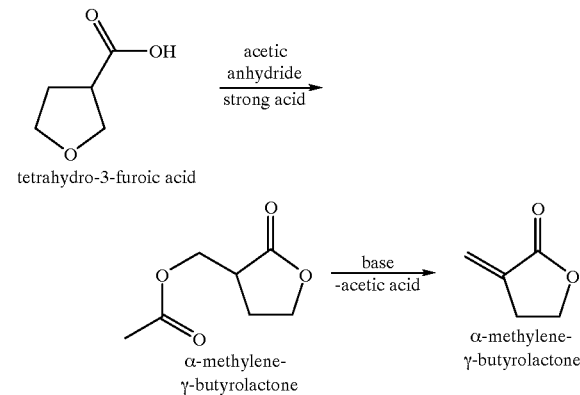
tetrahydro-3-furoic acid acetic anhydride
strong acid
→

α-methylene-γ-butyrolactone base
−acetic acid
→

α-methylene-γ-butyrolactone

Additionally the invention provides a novel compound, α-acetoxymethyl-γ-butyrolactone which may serve as an intermediate or starting material for the production of α-methylene-γ-butyrolactone (Scheme II) and is potentially useful in its own right as pre-polymer or polymer additive.

In the context of this disclosure, a number of terms and abbreviations shall be utilized for interpretation of the specification and the claims. The following definitions are provided.

"Nuclear magnetic resonance" is abbreviated NMR. "α-methylene-γ-butyrolactone" is abbreviated MBL "α-acetoxymethyl-γ-butyrolactone" is abbreviated AMB As used herein the term "a α-carboxylatomethyl-γ-butyrolactone" means a compound having the structure:

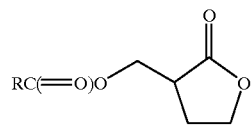

wherein RC(=O)O is a carboxylato group, for example if R=CH₃ then RC(=O)O is acetate.

As used herein the term "strong acid catalyst" means any Bronstead acid with a pKa<1, capable of catalyzing the conversion of tetrahydro-3-furoic acid or esters of tetrahydro-3-furoic acid to either AMB or MBL under suitable conditions.

The term "base or basic catalyst" or "strong base or basic catalyst" will refer to a basic catalyst useful in a low temperature, non-gas phase process for the production of α-methylene-γ-butyrolactone. These catalysts are typically acetates or carboxylates.

The term "gas phase base catalyst" refers to a basic catalyst used in a gas phase process for the production of α-methylene-γ-butyrolactone.

The term "furoic acid" as used herein will refer to the substituted furoic acids tetrahydro-3-furoic acid and esters of tetrahydro-3-furoic acid.

Furoic Acids

Furoic acids are useful as starting materials in the present invention, particularly tetrahydro-3-furoic acid and esters of tetrahydro-3-furoic acid. Suitable esters of tetrahydro-3-furoic acid include but are not limited to methyl tetrahydro-3-furoate, ethyl tetrahydro-3-furoate, propyl tetrahydro-3-furoate, butyl tetrahydro-3-furoate, and phenyl tetrahydro-3-furoate. The furoic acid may be provided in any state including solid, liquid or gaseous form, depending on the requirements of the reaction.

Acid Catalyst

The present invention provides an acidic catalyst for the conversion of tetrahydro-3-furoic acid to α-methylene-γ-butyrolactone or α-acetoxymethyl-γ-butyrolactone. Such catalysts are common and well known in the art. Suitable in the present invention are any Bronstead acids with a pKa<1, capable of catalyzing the conversion of tetrahydro-3-furoic acid or esters of tetrahydro-3-furoic acid to either AMB or MBL. For example suitable acids will include but are not limited to fluorosulfonic acid, trifluoromethanesulfonic acid, Nafion® perfluorocarbon sulfonic acid membrane, sulfuric acid, benzenesulfonic acid, toluenesulfonic acid and phosphoric acid. These acids may be used independently or jointly. A particularly useful acid catalyst is trifluoromethanesulfonic acid.

The amount of time required for complete conversion of the furoic acid starting material to product will vary with contact temperature. The temperature of the reaction for the conversion of tetrahydro-3-furoic acid to α-methylene-γ-butyrolactone can range from about 20° C. to about 400° C., where a range of about 100° C. to about 200° C. is particularly suitable. The temperature of the reaction for the conversion of tetrahydro-3-furoic acid to α-acetoxymethyl-γ-butyrolactone can range from about 20° C. to about 200° C., where a range of about 50° C. to about 120° C. is particularly suitable. Reaction times may vary from about 30 minutes under high temperature conditions to about 100 hours under less favorable temperature conditions. Typically reactions may be completed in about 1 to about 24 hours.

Base Catalyst and Gas Phase Base Catalyst

The present invention provides a basic catalyst for the conversion of α-acetoxymethyl-γ-butyrolactone, where acetic anhydride is an element of the reaction mixture, to α-methylene-γ-butyrolactone. Such catalysts are common and well known in the art. Where acetic anhydride is an element of the reaction mixture a suitable base catalyst is any base that will form an acetate upon reacting with acetic acid. In this context, suitable bases will be defined by the formula M(acetate)$_x$, where x is 1 or 2; M is a cation of charge +x, including but not limited to Li$^+$, Na$^+$, K$^+$, Rb$^+$, Cs$^+$, Mg$^{++}$, Ca$^{++}$, Sr$^{++}$, Ba$^{++}$, (CH$_3$)$_4$N$^+$, (C$_2$H$_5$)$_4$N$^+$, (CH$_3$)$_4$P$^+$, (C$_2$H$_5$)$_4$P$^+$ and 1-ethyl-3-methylimidazolium cations. Particularly suitable in the present invention are the bases tetramethylammonium acetate and 1-ethyl-3-methylimidazolium acetate.

Alternatively, where any acid anhydride is an element of the reaction the base will be defined by the formula, M(carboxylate)$_x$, where x is 1 or 2; M is a cation of charge +x including, but not limited to Li$^+$, Na$^+$, K$^+$, Rb$^+$, Cs$^+$, Mg$^{++}$, Ca$^{++}$, Sr$^{++}$, Ba$^{++}$, (CH$_3$)$_4$N$^+$, (C$_2$H$_5$)$_4$N$^+$, (CH$_3$)$_4$P$^+$, (C$_2$H$_5$)$_4$P$^+$ and 1-ethyl-3-methylimidazolium cations; and the carboxylate may include formate, acetate, propionate, benzoate, phthalate, poly(acrylate), succinate, monomethylsuccinate, 2,2'-dimethylsuccinate and 2,3-dimethylsuccinate. It will be appreciated that any of the aforementioned bases may be used independently or jointly to effect the desired conversion.

As with the acid catalyzed reactions the amount of time required for complete conversion of acetoxymethyl-γ-butyrolactone to α-methylene-γ-butyrolactone will vary with contact temperature. Typically temperature of the reaction can range from about 40° C. to about 200° C., where a range of about 60° C. to about 140° C. is particularly suitable.

In an alternate embodiment the present invention provides a gas phase process for the production of α-methylene-γ-butyrolactone where a gaseous furoic acid is passed over a gas phase base catalyst at high temperature. In this embodiment suitable temperatures may range from about 100° C. to about 600° C. Suitable gas phase base catalysts may include but are not limited to magnesium oxide, calcium oxide, strontium oxide, barium oxide, magnesium hydroxide, calcium hydroxide, cadmium oxide, potassium hydroxide, strontium hydroxide, rubidium oxide, sodium hydroxide, lithium hydroxide and barium hydroxide. The gas phase catalysts may be used individually or in any combination, or may optionally be supported on a variety of supports. Suitable supports are well known in the art and may include, but are not limited to silica, titania, zirconia, alumina and various zeolites.

Acid Anhydride

The present invention provides an acid anhydride for the conversion of tetrahydro-3-furoic acid or esters of tetrahydro-3-furoic acid to "α-carboxylato-methyl-γ-butyrolactone". When the acid anhydride is acetic anhydride, the product is α-acetoxymethyl-γ-butyrolactone. From this point the α-carboxylato-methyl-γ-butyrolactone or α-acetoxymethyl-γ-butyrolactone may be converted to end product either via the use of a base catalyst (discussed above) or by thermolysis at temperatures in the range of 100° C. to 400° C. Such anhydrides are common and well known in the art. In the context of the present invention, suitable anhydrides will include but are not limited to acetic anhydride, formic-acetic anhydride, propionic anhydride, benzoic anhydride, phthalic anhydride, anhydrides of poly(acrylic acid), succinic anhydride, monomethylsuccinic anhydride, 2,2'-dimethylsuccinic anhydride and 2,3-dimethylsuccinic anhydride. The preferred acid anhydride is acetic anhydride. Phthalic anhydride, anhydrides of poly(acrylic acid), succinic anhydride, monomethylsuccinic anhydride, 2,2'-dimethylsuccinic anhydride and 2,3-dimethylsuccinic anhydride all offer the possibly advantageous feature that the corresponding acids, which form during the course of the reaction, can be thermally dehydrated to recover the anhydride.

The skilled person will recognize that optimization of any catalytic conversion will involve determination of a specific ratio of catalyst to starting material, and methods for determining such ratios are well established in the art. In the context of the present invention for the production of MBL the ratio of furoic acid reactant to the acid catalyst will range from about 1:1,000 to about 10,000:1 w/w where a ratio of about 1000:1 w/w is suitable.

Similarly, where an acid anhydride is an element of the reaction the ratio of the furoic acid starting material and acid anhydride may range from about 10:1 to about 1:10,000 w/w where a range of about 1:1 to about 1:10,000 w/w is suitable.

Segregated Acid Catalyst and Base Catalyst

In one embodiment of the invention the conversion of tetrahydro-3-furoic acid to ABM or MBL was accomplished in a common vessel under conditions whereby the acid and base catalysts were segregated. Ordinarily, combining a strong acid catalyst with a basic catalyst results in immediate neutralization and loss of catalytic activity. However, this difficulty may be overcome if the acid catalyst and basic catalyst are separately maintained on segregated supports. In this fashion each catalyst maintains its individual catalytic activity without complete neutralization.

In the context of the present invention, Nafion® perfluorocarbon sulfonic acid membrane was used as the requisite acid catalyst and acetate-loaded anion exchange resin (for example, Dowex® 1X8-100 beads) was used as the requisite basic catalyst in a single vessel conversion of tetrahydro-3-furoic acid to both ABM and MBL. Good conversions were observed for both products as indicated in Example 12.

Reaction Conditions and Processes

The present method lends itself to either batch or continuous processes. A continuous process employs a pipeline reactor for the tetrahydro-3-furoic acid to α-methylene-γ-butyrolactone conversion. Liquid tetrahydro-3-furoic acid is fed into a pipe containing a catalyst bed where the reaction occurs to make α-methylene-γ-butyrolactone. Any off-gases are vented out the end of the pipeline and the α-methylene-γ-butyrolactone product falls out as a liquid. If needed, the mixture can be fed into the pipeline again to increase the overall conversion to α-methylene-γ-butyrolactone.

Alternatively, the reaction can run under continuous flow conditions, where water is constantly removed from the reaction medium and neither starting tetrahydro-3-furoic acid nor product α-methylene-γ-butyrolactone is allowed to be present in concentration great enough for rapid polymerization.

Recovery Methods

α-methylene-γ-butyrolactone, may be recovered using techniques common to the art. For example, when allowed to cool the α-methylene-γ-butyrolactone reaction mixture, forms a viscous, clear mass. Alternatively, when heated under vacuum, the α-methylene-γ-butyrolactone mixture can be distilled directly from the reaction mixture. Additionally, the reaction mixture can be dissolved in water, adjusted to pH=4 with 6N HCl, then distilled. Similarly, the separation of α-methylene-γ-butyrolactone from byproducts can be accomplished using vacuum distillation with a spinning band column. Another method to recover the desired product is to polymerize α-methylene-γ-butyrolactone using standard free-radical polymerization, isolate the polymer by precipitation from methanol, then thermally depolymerize back to α-methylene-γ-butyrolactone by heating under vacuum. Finally, α-methylene-γ-butyrolactone may also be separated from byproducts by melt crystallization.

α-Acetoxymethyl-γ-butyrolactone may be recovered by distillation methods comparable to distillation methods discussed above for the isolation of MBL. α-Acetoxymethyl-γ-butyrolactone is relatively stable and has been distilled in vacuum at temperatures less than about 140° C. to afford a colorless oil which crystallizes upon cooling and standing to a white crystalline compound, but it can thermolyze to α-methylene-γ-butyrolactone and darkly-colored residue when heated much above that temperature. Given that pure α-acetoxymethyl-γ-butyrolactone crystallizes at room temperature, care must be taken during its distillation to avoid plugging the condenser. The molecular structure of α-acetoxymethyl-γ-butyrolactone as determined by single crystal X-ray diffraction revealed no extraordinary features.

The identification of AMB was confirmed after purification by NMR and revealed the following spectral data:

$^1$H NMR (500 MHz, CD$_2$Cl$_2$) δ2.06 (s, 3H), 2.2 (m, 1H), 2.4 (m, 1H), 2.9 (m, 1H), 4.25 (m, 2H), 4.38 (m, 2H); $^{13}$C NMR (125 MHz, CD$_2$Cl$_2$) δ21.1, 26.3, 39.8, 63.1, 67.4, 171.1, 177.1. $^1$H NMR spectra are reported in ppm downfield from tetramethylsilane; s=singlet and m=multiplet. Anal. Calcd. for C$_7$H$_{10}$O$_4$: C, 53.16%; H, 6.37. Found C, 53.12; H, 6.46.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

General Methods

Common reagents were purchased from Sigma α-Aldrich and solvents from VWR Scientific. NMR spectra were recorded on Varian VXR-500, GE QE-300, and Bruker 300 MHz spectrometers.

The meaning of abbreviations is as follows: "μL" means microliter, "mL" means milliliter(s), "L" means liter(s), "mM" means millimolar, "M" means molar, "mmol" means millimole(s) "w/w" means weight to weight and "ng" means nanogram(s).

Pure α-methylene-γ-butyrolactone was synthesized using the method reported by Murray (*Synthesis* 1:35–38 (1985)). α-Methylene-γ-butyrolactone was purified by distillation at 0.5 torr/65° C. to give a colorless liquid: $^1$H NMR (500 MHz, CDCl$_3$) δ2.9 (m, 2H), 4.3 (t, J=5.2, 2H), 5.6 (t, J=2.5, 1H), 6.2 (t, J=3.2, 1H); $^{13}$C NMR (125 MHz, CDCl$_3$) δ171.49, 134.40, 122.98, 66.06, 28.16. $^1$H NMR spectra are reported in ppm downfield from tetramethylsilane; t=triplet, and m=multiplet.

Preparation of 8% Ba(OH)$_2$/SiO$_2$:

50 g of granular, sol-gel derived silica (+8 mesh; 300 m$^2$g$^{-1}$) was slurried into a solution of 10 g Ba(OH)$_2$ octahydrate in 100 mL distilled water. The slurry was stirred for 10 min and then evaporated to dryness. The recovered solid was dried in a gold boat under flowing (100 mL/min) nitrogen at 550° C. for 2 h and then collected under nitrogen as a granular white solid.

Example 1

Acid-Catalyzed Preparation of α-Methylene-γ-butyrolactone from Neat Tetrahydro-3-furoic Acid Neat tetrahydro-3-furoic acid (1 mL, approximately 1.2 g, 10 mmol) was heated with trifluoromethanesulfonic acid (0.1 g, 0.67 mmol) in an NMR tube to approximately 160° C. After 5.5 h, small amounts of α-methylene-γ-butyrolactone could be detected. After about 68 h the mixture was vacuum-distilled and the distillate found to contain α-methylene-γ-butyrolactone in amount corresponding to about 5–10% yield based on tetrahydro-3-furoic acid.

Example 2

Acid-Catalyzed Preparation of α-Methylene-γ-Butyrolactone from Tetrahydro-3-Furoic Acid A mixture of tetrahydro-3-furoic acid (0.20 g, 1.7 mmol) trifluoro-methanesulfonic acid (0.05 g, 0.33 mmol), and 1-ethyl-3-methylimidazolium trifluoromethanesulfonate (1.0 g) was heated to about 200° C. After about 30 min, the conversion to α-methylene-γ-butyrolactone was about 50%. An additional 0.3 g (2.6 mmol) tetrahydro-3-furoic acid was added to this mixture, the temperature was raised to about 220° C., and about 0.2 g distillate was collected by condensation on a water-cooled condenser. By NMR analysis the distillate was approximately 60–65 mole % α-methylene-γ-butyrolactone, 30–35 mole % water, and less than 10 mole % unidentified compounds, representing an approximate recovered yield of 0.18 g (1.8 mmol) α-methylene-γ-butyrolactone or 42% based on starting tetrahydro-3-furoic acid.

After the distillation, a polymeric deposit was observed above the ionic liquid. This deposit upon thermolysis provided small amounts of α-methylene-γ-butyrolactone and starting tetrahydro-3-furoic acid, suggesting it may be a mixed polymer containing both polyether and polyester groupings.

Example 3

Acid-Catalyzed Preparation of α-Methylene-γ-butyrolactone from Tetrahydro-3-furoic Acid Under a nitrogen purge, a mixture of liquid 1-ethyl-3-methylimidazolium trifluoromethanesulfonate (2.0 g) and trifluoromethanesulfonic acid (0.1 g, 0.67 mmol) was heated to approximately 300° C. (external temperature). Tetrahydro-3-furoic acid (total of 6 g, 52 mmol) was added over a period of 2.5 h, sometimes dropwise and sometimes in greater amounts, while the exit stream was cooled to approximately 0° C. A total of 3.1 g condensate was collected from the exit stream and determined to be approximately 65 weight % α-methylene-γ-butyrolactone, 25 weight % water, and about 10 weight % unidentified compound(s), representing a recovered yield of 2 g (20 mmol) α-methylene-γ-butyrolactone, about 38% based on starting tetrahydro-3-furoic acid.

Example 4

Acid-Catalyzed Preparation of α-Methylene-γ-butyrolactone from Tetrahydro-3-furoic Acid Tetrahydro-3-furoic acid (1.40 g, 12 mmol) was heated in sulfuric acid (11.3 g) to 150° C. for 2 h and then put under vacuum and heated further (external temperature 300° C.). Water but no α-methylene-γ-butyrolactone was evolved. After cooling, the sulfuric acid solution was quenched in aqueous KHCO$_3$ and the solution extracted with ether. The dried ether extract provided reasonably pure (α-methylene-γ-butyrolactone in about 26% recovered yield (0.31 g crude material, approximately 3.2 mmol).

Example 5

Acid-Catalyzed Preparation of α-Methylene-γ-butyrolactone from Tetrahydro-3-furoic Acid A 20 weight % solution of tetrahydro-3-furoic acid in sulfuric acid was separated into 4 portions. One portion was kept "neat", the second treated with approximately 10 weight % water, the third with approximately 30 weight % water and the fourth with approximately 50 weight % water. All were heated to 125–130° C. and periodically analyzed. α-Methylene-γ-butyrolactone was formed in each reaction, but additional compound(s) also were formed. The approximate yield of α-methylene-γ-butyrolactone can be seen in Table 1.

TABLE 1

| medium | yield of α-methylene-γ-butyrolactone | | |
|---|---|---|---|
|  | 5 h | 11 h | 26 h |
| "neat" | 45% |  |  |
| 10 weight % water | 48% | 30% |  |
| 30 weight % water | 15% | 36% | 48% |
| 50 weight % water | not observable | 5% | 12% |

From this example it appears that 1) water, which is a coproduct of the formation of α-methylene-γ-butyrolactone, suppresses the reaction and 2) prolonged heating in sulfuric acid apparently does convert α-methylene-γ-butyrolactone to other unknown compound(s).

Example 6

Preparation of α-Acetoxymethyl-γ-butyrolactone

A mixture of tetrahydro-3-furoic acid (4.4 g, 38 mmol), acetic anhydride (9.3 g, 91 mmol) and TiCl$_2$(SO$_3$CF$_3$)$_2$ (0.1 g, 0.24 mmol) was allowed to stir at 30° C. overnight. The resulting mixture was then heated to approximately 90–95° C. and then evaporated to provided 6.9 g crude yield of α-acetoxymethyl-γ-butyrolactone. The crude material was vacuum-distilled (0.4–0.5 torr). The fraction boiling at 120–123° C. was pure α-acetoxymethyl-γ-butyrolactone by NMR analysis. Allowing the distillation temperature to increase to above 145° C. caused massive decomposition of the material in the still pot and α-methylene-γ-butyrolactone and other compound(s) appeared in the distillate.

Example 7

Preparation of α-Acetoxymethyl-γ-butyrolactone

To a mixture of tetrahydro-3-furoic acid (2.0 g, 17 mmol) and acetic anhydride (6.0 g, 59 mmol) was added trifluoromethansulfonic acid (0.05 g, 0.33 mmol). The resulting mixture was allowed to stir at room temperature for 4 h. Evaporation of the resulting mixture afforded an oil. NMR analysis of this oil showed that at least 90% of the starting tetrahydro-3-furoic acid had been converted to α-acetoxymethyl-γ-butyrolactone.

Example 8

Base-Catalyzed Preparation of α-Methylene-γ-butyrolactone from α-Acetoxymethyl-γ-butyrolactone With a liquid nitrogen trap, a mixture of 1-ethyl-3-methylimidazolium acetate (0.47 g) and α-acetoxymethyl-γ-butyrolactone (1.16 g, 7.3 mmol) was heated for 30 min under vacuum at 100–120° C. A total of 0.65 g of material was collected from the trap and NMR analysis showed that it consisted of α-methylene-γ-butyrolactone (approximately 55 mole %; 67 weight %; 4.4 mmol; 60% yield based on starting α-acetoxymethyl-γ-butyrolactone), acetic acid (approximately 45 mole %; 33 weight %) and small amounts of additional compound(s).

Example 9

Base-Catalyzed Preparation of α-Methylene-γ-butyrolactone from α-Acetoxymethyl-γ-butyrolactone 1-Ethyl-3-methylimidazolium acetate (8.8 g) was heated under vacuum through sequential cold-water and liquid-nitrogen traps. Crude α-acetoxymethyl-γ-butyrolactone (obtained by vacuum concentration from $TiCl_2(SO_3CF_3)_2$-catalyzed reaction of tetrahydro-3-furoic acid (11.4 g, 98 mmol) and acetic anhydride (20 g)) was added dropwise over 4 h to the hot medium, which was kept at 95–125° C. The water-cooled trap collected 4.83 g of very pure α-methylene-γ-butyrolactone and the liquid nitrogen trap collected 9.36 g of a mixture of α-methylene-γ-butyrolactone, acetic acid and water. The estimated recovery of α-methylene-γ-butyrolactone was 7.3 g or 76% of theoretical based on starting tetrahydro-3-furoic acid. The combined condensates were collected and redistilled, providing 5.15 g pure α-methylene-γ-butyrolactone (52.5 mmol, 53% yield based on starting tetrahydro-3-furoic acid).

Example 10

Acid-Catalyzed Preparation of α-Methylene-γ-butyrolactone from Tetrahydro-3-furoic Acid and Phthalic Anhydride To a mixture of tetrahydro-3-furoic acid (1.16 g, 10 mmol) and phthalic anhydride (1.50 g, 10 mmol) was added trifluoromethanesulfonic acid (0.01 g, 0.067 mmol). The resulting mixture was heated to melt (estimated temperature of 130–150° C.; the literature melting temperature of phthalic anhydride is 134° C.). After 5 min, the mixture was allowed to cool and sampled for NMR analysis (pyridine-d5). The NMR spectrum showed evidence of several compounds, including unreacted tetrahydro-3-furoic acid and/or its mixed anhydride with phthalic acid, and a trace of α-methylene-γ-butyrolactone (NMR 5.5 t, 6.1 t). The remainder of the mixture was heated again to melt, estimated temperature 130–140° C., for 30 min, allowed to cool, and sampled for NMR analysis (pyridine-d5, tetrahydrofuran-d8). Again several compounds were present, including approximately 44% α-methylene-γ-butyrolactone.

Example 11

Acid-Catalyzed Preparation of α-Methylene-γ-butyrolactone from Tetrahydro-3-furoic acid and 2,2'-Dimethylsuccinic Anhydride 2,2'-Dimethylsuccinic acid was heated to melt under nitrogen atmosphere until the apparent evolution of moisture ceased, then was heated under vacuum to remove most of the remaining moisture. The resulting material had a NMR spectrum noticeably different from that of the starting acid, consistent with formation of significant amounts of 2,2'-dimethylsuccinic anhydride.

The above prepared 2,2'-dimethylsuccinic anhydride (1.88 g) was mixed with tetrahydro-3-furoic acid (1.16 g, 10 mmol) and trifluoromethanesulfonic acid (0.008 g) to make a homogeneous liquid. The resulting mixture was stirred overnight at room temperature. The NMR spectrum of a sample taken from this overnight mixture showed no evidence for reaction.

The mixture was then heated under nitrogen atmosphere. After heating for 3.5 h at 65–70° C. and 3.5 h at 90–95° C., the NMR spectrum of a sample revealed the presence of a new compound, whose NMR spectrum was consistent with that expected for the dimethylsuccinate ester of hydroxymethylbutyrolactone. The material was heated an additional 2 days at 90–95° C. and sampled again for NMR analysis, which revealed approximately 5% unreacted tetrahydro-3-furoic acid, approximately 90–95% putative (dimethylsuccinatomethyl)butyrolactone, and approximately 2–4% α-methylene-γ-butyrolactone. This mixture was subsequently treated with tetramethylammonium acetate (0.2 g) and heated with a bubbling nitrogen purge to 200–220° C. for about 2 h. The purge stream was cooled in a dry ice trap and contained 0.64 g of clear liquid, which when sampled for NMR analysis was largely α-methylene-γ-butyrolactone and water with lesser amounts of additional unidentified compound(s).

Example 12

Preparation of α-Methylene-γ-butyrolactone from Segregated Acid Catalyst and Base Catalyst A "stock solution" was prepared containing 3.78 g tetrahydro-3-furoic acid and 11.76 g acetic anhydride. 4.09 g of this "stock solution" was put into a vessel together with a piece of Nafion® perfluorocarbon sulfonic acid membrane weighing 0.36 g. The mixture was heated for 19 h at 60–70° C. then analyzed by NMR, revealing virtually complete conversion of the starting tetrahydro-3-furoic acid to α-acetoxymethyl-γ-butyrolactone.

Separately, 1.35 g of the "stock solution" was put into a vessel together with a piece of Nafion® perfluorocarbon sulfonic acid membrane weighing 0.26 g, and 0.42 g acetate-loaded anion exchange resin (Dowex® 1X8-100 beads). This mixture was heated for 19 h at 60–70° C. then analyzed by NMR, revealing virtually complete conversion of the starting tetrahydro-3-furoic acid to a mixture of α-acetoxymethyl-γ-butyrolactone (approximately 74 mole %) and α-methylene-γ-butyrolactone (approximately 26 mole % based on starting tetrahydro-3-furoic acid). Continued heating for an additional 20 h at 60–70° C. resulted in an increased conversion of the α-acetoxymethyl-γ-butyrolactone (now approximately 65 mole %) to α-methylene-γ-butyrolactone (now approximately 35 mole % based on starting tetrahydro-3-furoic acid).

As a control, 5.5 g of the "stock solution" alone was heated for 39 h at 60–70° C., after which NMR analysis revealed no conversion of tetrahydro-3-furoic acid to either α-acetoxymethyl-γ-butyrolactone or α-methylene-γ-butyrolactone.

Example 13

Base-Catalyzed Preparation of α-Methylene-γ-butyrolactone from Tetrahydro-3-furoic Acid A ¼ inch reactor was packed with a 1.0 g charge of 8% $Ba(OH)_2/SiO_2$ and heated to 340° C. The tetrahydro-3-furoic acid was then delivered to the reactor at a flowrate of 0.5 cc/h coupled with a nitrogen flow rate of 12 cc/min. Over the course of 3 h, the exiting vapor was trapped in a cold trap. Gas chromatography/mass spectrometry analysis revealed that a conversion of 98% of the tetrahydro-3-furoic acid had occurred giving a 38% yield of α-methylene-γ-butyrolactone. The major byproducts, amounting to less than approximately 10% of the converted reactant, were γ-butyrolactone and α-methyl-γ-butyrolactone.

What is claimed is:

1. A process for preparing α-methylene-γ-butyrolactone comprising heating a mixture of a furoic acid selected from the group consisting of tetrahydro-3-furoic acid and esters of tetrahydro-3-furoic acid and a strong acid catalyst under conditions whereby α-methylene-γ-butyrolactone is formed and optionally recovering the α-methylene-γ-butyrolactone.

2. The process of claim 1 wherein the furoic acid and the strong acid catalyst are heated at a temperature of from about 20° C. to about 400° C.

3. The process of claim 2 wherein the temperature is from about 100° C. to about 200° C.

4. The process of claim 1 wherein the strong acid catalyst is selected from the group consisting of fluorosulfonic acid, trifluoromethanesulfonic acid, sulfuric acid, benzenesulfonic acid, toluenesulfonic acid and phosphoric acid.

5. The process of claim 1 wherein the furoic acid and strong acid catalyst are combined in a ratio of furoic acid:strong acid catalyst of from about 1:1,000 to about 1,000:1 w/w.

6. The process of claim 1 where the strong acid catalyst is a perfluorocarbon sulfonic acid membrane and the furoic acid:perfluorocarbon sulfonic acid membrane ratio is from about 1:1,000 to about 10,000:1 w/w.

7. The process of any of claim 1, 2, 4 or 6 wherein the furoic acid is tetrahydro-3-furoic acid.

8. The process of any of claim 1, 2, 4 or 6 wherein the furoic acid is an ester of tetrahydro-3-furoic acid.

9. A process for preparing α-acetoxymethyl-γ-butyrolactone comprising heating a mixture of a furoic acid selected from the group consisting of tetrahydro-3-furoic acid and esters of tetahydro-3-furoic acid, with acetic anhydride and a strong acid catalyst under conditions wherein α-acetoxymethyl-γ-butyrolactone is formed and optionally recovering the α-acetoxymethyl-γ-butyrolactone.

10. The process of claim 9 wherein the furcic acid, acetic anhydride and a strong acid catalyst are heated from about 20° C. to about 200° C.

11. The process of claim 10 wherein the furoic acid, acetic anhydride and a strong acid catalyst are heated from about 50° C. to about 120° C.

12. The process of claim 9 wherein the strong acid catalyst is selected from the group consisting of trifluoromethanesulfonic acid, sulfuric acid, benzenesulfonic acid, toluenesulfonic acid, phosphoric acid and perfluorocarbon sulfonic acid membrane.

13. The process of claim 9 wherein the furoic acid and strong acid catalyst are combined in a ratio of furoic acid:strong acid catalyst from about 1:1,000 to about 10,000:1 w/w, and wherein the furoic acid:acetic anhydride ratio is from about 10:1 to about 1:10,000 w/w.

14. The process of any of claim 9, 10, 12 or 13 wherein the furoic acid is tetrahydro-3-furoic acid.

15. The process of any of claim 9, 10, 12 or 13 wherein the furoic acid is an ester of tetrahydro-3-furoic acid.

16. The product produced by of the process of any of claim 9, 11, 10, 12 or 13.

17. An α-acetoxymethyl-γ-butyrolactone composition according to the formula:

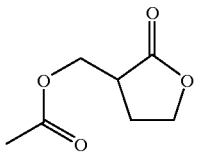

18. A process for preparing α-methylene-γ-butyrolactone comprising heating a mixture of α-acetoxymethyl-γ-butyrolactone and base catalyst under conditions whereby α-methylene-γ-butyrolactone is formed and optionally recovering the α-methylene-γ-butyrolactone.

19. The process of claim 18 wherein the α-acetoxymethyl-γ-butyrolactone and base catalyst are heated at a temperature of from about 40° C. to about 200° C.

20. The process of claim 18 wherein the α-acetoxymethyl-γ-butyrolactone and base catalyst are heated at a temperature of from about 60° C. to about 120° C.

21. The process of claim 18 wherein the base catalyst is any base which forms an acetate when reacted with acetic acid.

22. The process of claim 21 wherein the base catalyst is defined according to the formula, M(acetate)$_x$;

wherein x is an integer selected from the group consisting of 1 and 2; and

M is a cation of charge +x selected from the group consisting of Li$^+$, Na$^+$, K$^+$, Rb$^+$, Cs$^+$, Mg$^{++}$, Ca$^{++}$, Sr$^{++}$, Ba$^{++}$, (CH$_3$)$_4$N$^+$, (C$_2$H$_5$)$_4$N$^+$, (CH$_3$)$_4$P$^+$, (C$_2$H$_5$)$_4$P$^+$ and 1-ethyl-3-methylimidazolium cation.

23. The process of claim 22 wherein the base is selected from the group consisting of tetramethylammonium acetate and 1-ethyl-3-methylimidazolium acetate.

24. A process for preparing α-methylene-γ-butyrolactone comprising:

(a) combining a furoic acid selected from the group consisting of tetrahydro-3-furoic acid and an ester of tetrahydro-3-furoic acid with an acid anhydride and a strong acid catalyst under conditions whereby a α-carboxylatomethyl-γ-butyrolactone is formed;

(b) heating the product of step (a) under conditions whereby α-methylene-γ-butyrolactone is formed; and (c) optionally recovering the α-methylene-γ-butyrolactone.

25. The process of claim 24 wherein the combining of step (a) is conducted at a temperature from about 20° C. to about 200° C.

26. The process of claim 24 wherein the heating of step (b) is conducted at a temperature from about 100° C. to about 400° C.

27. The process of claim 24 wherein the acid anhydride is selected from the group consisting of acetic anhydride, formic-acetic anhydride, propionic anhydride, benzoic anhydride, phthalic anhydride, anhydrides of poly(acrylic acid), succinic anhydride, monomethylsuccinic anhydride, 2,2'-dimethylsuccinic anhydride and 2,3-dimethylsuccinic anhydride.

28. The process of claim 24 wherein at step (b) the product of step (a) is heated in the presence of a base catalyst at a temperature of about 40° C. to about 200° C.

29. The process of claim 28 wherein the base catalyst is defined according to the formula, M(carboxylate)$_x$;

wherein x is an integer selected from the group consisting of 1 and 2; and

M is a cation of charge +x chosen from the group consisting of Li$^+$, Na$^+$, K$^+$, Rb$^+$, Cs$^+$, Mg$^{++}$, Ca$^{++}$, Sr$^{++}$, Ba$^{++}$, (CH$_3$)$_4$N$^+$, (C$_2$H$_5$)$_4$N$^+$, (CH$_3$)$_4$P$^+$, (C$_2$H$_5$)$_4$P$^+$ and 1-ethyl-3-methylimidazolium cation; and carboxylate is selected from the group consisting of formate, acetate, propionate, benzoate, phthalate, poly (acrylate), succinate, monomethylsuccinate, 2,2'-dimethylsuccinate and 2,3-dimethylsuccinate.

30. The process of claim 24 wherein the strong acid catalyst is selected from the group consisting of trifluoromethanesulfonic acid, sulfuric acid, benzenesulfonic acid, toluenesulfonic acid, phosphoric acid and perfluorocarbon sulfonic acid membrane.

31. The process of claim 24 wherein the furoic acid and strong acid catalyst are combined in a ratio of furoic acid:strong acid catalyst from about 1:1,000 to about 10,000:1 w/w.

32. The process of claim 24 wherein the furoic acid:acid anhydride ratio is from about 100:1 to about 1:10,000 w/w.

33. The process of claim 24 wherein the strong acid catalyst is a perfluorocarbon sulfonic acid membrane and the base catalyst is an acetate loaded anion exchange resin.

34. The process of claim 24 wherein the furoic acid is tetrahydro-3-furoic acid.

35. The process of claim 24 wherein the furoic acid is an ester of tetrahydro-3-furoic acid.

36. A process for preparing α-methylene-γ-butyrolactone comprising heating a mixture of a gaseous furoic acid selected from the group consisting of tetrahydro-3-furoic acid and esters of tetrahydro-3-furoic acid and a gas phase base catalyst under conditions whereby α-methylene-γ-butyrolactone is formed and optionally recovering the α-methylene-γ-butyrolactone.

37. The process of claim 36 wherein the gaseous furoic acid and the gas phase base catalyst are heated at a temperature from about 100° C. to about 600° C.

38. The process of claim 36 wherein the gas phase base catalyst is selected from the group consisting of magnesium oxide, calcium oxide, strontium oxide, barium oxide, magnesium hydroxide, calcium hydroxide, cadmium oxide, potassium hydroxide, strontium hydroxide, rubidium oxide, sodium hydroxide, lithium hydroxide and barium hydroxide.

39. The process of claim 37 wherein the gas phase base catalyst is optionally supported on a suitable support.

40. The process of claim 39 wherein the suitable support is selected from the group consisting of silica, titania, zirconia, alumina and various zeolites.

* * * * *